United States Patent [19]

Yoshimura et al.

[11] Patent Number: 5,227,147

[45] Date of Patent: Jul. 13, 1993

[54] APATITE WHISKER AND METHOD FOR PREPARATION THEREOF

[75] Inventors: Masahiro Yoshimura, 1-6-12, Teraonaka, Ayase-shi, Kanagawa-ken; Koji Ioku, Kawasaki; Kengo Okamoto, Yokozemachi; Hiroyasu Takeuchi, Hanno, all of Japan

[73] Assignees: Mitsubishi Materials Corp.; Masahiro Yoshimura, Tokyo, Japan

[21] Appl. No.: 794,870

[22] Filed: Nov. 19, 1991

[51] Int. Cl.$^5$ ............................................. C01B 25/26
[52] U.S. Cl. ..................................... 423/308; 423/309; 423/311
[58] Field of Search ................ 424/675; 423/308, 309, 423/311

[56] References Cited

U.S. PATENT DOCUMENTS

| | | | |
|---|---|---|---|
| 2,546,305 | 3/1951 | Jaffe et al. | 423/308 |
| 4,481,175 | 11/1984 | Iino et al. | 423/311 |
| 5,073,357 | 12/1991 | Takagi et al. | 423/311 |

OTHER PUBLICATIONS

Della M. Roy, "Crystal Growth of Hydroxyapatite", *Mat. Res. Bull.* vol. 6, No. 12, pp. 1337–1340 (1971), Pergamon Press, Inc.

*Primary Examiner*—Wayne Langel
*Attorney, Agent, or Firm*—Malcolm B. Wittenberg

[57] ABSTRACT

An apatite whisker has a mean aspect ratio (length along c-axis/length along a-axis) of not less than 10.0 and contains a carbonic acid group of not less than 0.01 wt. % based on total weight of the whisker. A method for preparing an apatite whisker involves precipitating and growing an apatite from a liquid containing phosphoric acid and calcium to have a mean aspect ratio (length along c-axis/length along a-axis) of not less than 10.0.

19 Claims, No Drawings

APATITE WHISKER AND METHOD FOR PREPARATION THEREOF

BACKGROUND OF THE INVENTION

This invention relates to an apatite whisker useful as a packed stationary phase employed in a column for column chromatography, a biotechnological material, such as a carrier for cell cultivation or isolation, or as a variety of fiber-reinforced composite materials or building materials as substitution materials for asbestos, and a method for preparation thereof.

As a method for preparing hydroxyapatite particles used as a biotechnological material, referred to hereinafter as HAp particles, there has hitherto proposed in, for example, Japanese Laid-open Patent Application No. 63-284 (1988), a method for preparing HAp fibers composed of HAp crystal aggregates, comprising uniformly dispersing HAp in an aqueous solution of a water-soluble high polymer, extruding the resulting liquid dispersion through a die composed of an array of spinneret nozzles, and molding and baking the extruded mass. There has also been proposed in Japanese Laid-open Patent Application No. 61-242968 (1986) a method for preparing HAp crystal particles as primary particles in the form of hexagonal prisms having an aspect ratio of 2.5 to 3.0 by carrying out hydrocuring reaction in an autoclave under pressure.

However, none of the HAp particles prepared by the above methods can be termed whiskers as far as their shape is concerned. These HAp particles are disadvantageous in that, if they are used as a carrier for cell cultivation, superior separating and spreading properties can not be developed, and that, if they are used as a fiber-reinforced composite material, the effect proper to the whiskers in improving the mechanical strength of the material can also not be produced.

On the other hand, silicon carbide and silicon nitride whiskers are used extensively industrially as reinforcing whiskers in a fiber-reinforced composite material, while asbestos is used extensively as a structural material for building or construction. However, these silicon carbide or nitride whiskers or asbestos presents serious problems with respect to hygienic safety because of the inherent chemical toxicity or cancerogenic properties due to the shape of the whiskers.

SUMMARY OF THE INVENTION

It is a principal object of the present invention to provide a novel apatite whisker capable of separating and developing substances in higher accuracy and having toughness so as to be used as a variety of fiber reinforced materials.

The above and other objects of the present invention will become apparent from the following description.

In accordance with the present invention, there is provided an apatite whisker having a mean aspect ratio (length along c-axis/length along a-axis) of not less than 10.0 and containing a carbonic acid group of not less than 0.01 wt. % based on the total weight of the whisker.

In accordance with the present invention, there is also provided a method for preparing an apatite whisker comprising precipitating and growing an apatite from a liquid containing phosphoric acid and calcium to have a mean aspect ratio (length along c-axis/length along a-axis) of not less than 10.0.

PREFERRED EMBODIMENTS OF THE INVENTION

The present invention will be explained in more detail hereinbelow.

The HAp whisker of the present invention may be used as a packed stationary phase in a column having a superior cell separation or cultivating efficiency, as a biotechnological material, such as carrier for cell cultivation or separation, as a variety of fiber-reinforced composite materials, or as a substitute construction material for asbestos without harmful effects on living bodies. With the HAp whisker of the present invention, the a-plane or the b-plane of a fine HAp particle on which the phosphoric acid groups of the fine HAp particle are present in a major quantity, are grown selectively, in other words, the crystal is grown selectively along its c-axis, so as to provide a c-axis/a-axis length ratio or aspect ratio of 10.0 or higher in average, and carbonic acid groups are present in a specific amount. If the mean aspect ratio is lower than 10, the rate of adsorption is lowered when the whisker is used as a packed stationary phase in a column, while a sufficient strength cannot be developed when the whisker is used in a variety of fiber-reinforced composite materials or in a construction material in substitution for asbestos.

According to the present invention, the a-plane of the fine crystal is a plane defined by the b-axis and the c-axis, while the b-plane of the fine crystal is a plane defined by the a-axis and the c-axis if the hexagonal crystal is defined by with lattice vectors a, b, and c.

The lengths of the a-axis and the c-axis of the apatite whisker of the present invention may preferably be selected in such a manner as to facilitate the granulating process and to prevent clogging when the whiskers are used as the stationary packing phase in a column as well as to prevent the strength from being lowered when the whisker is in the form of fibers. Thus, the lengths of the crystal along the a-axis and along the c-axis may preferably be set so as to be in the ranges of from 0.1 to 10 $\mu$m and from 1 to 1000 $\mu$m, respectively.

According to the present invention, the amount of the carbonic acid groups is in a range not lower than 0.01 wt. % based on the total weight of the whisker. The upper limit of the carbonic acid group content may preferably be 5 wt. % or less, although the upper limit is not set specifically. If the amount of the carbonic acid groups is less than 0.01 wt. %, the produced crystals are not grown significantly along the c-axis so that the whisker shape is not achieved.

The method for the preparation of the apatite whisker according to the present invention will be explained in more detail.

In one aspect of the present invention, the method for the preparation of an apatite whisker comprises precipitating and growing an apatite from a liquid containing phosphoric acid and calcium, such as a slurry or solution of calcium phosphate compound(s) containing additive(s), a mixed slurry or solution of inorganic calcium compound(s), additive(s) and inorganic phosphoric acid compound(s), a mixed slurry or solution of organic calcium compound(s) and inorganic phosphoric acid compound(s) or a mixed slurry or solution of organic phosphoric acid compound(s) and inorganic calcium compound(s), so as to have a mean aspect ratio (length along c-axis/length along a-axis) of not less than 10.0.

As the calcium phosphate compounds which may be employed in the method of the present invention, those which may be converted easily into hydroxyapatite, such as hydroxy apatite, tricalcium phosphate, brucite or monetite, are preferred.

As the inorganic calcium compounds which may be employed in the method of the present invention, those which are reacted with and readily dissolved into additives, such as calcium hydroxide, calcium nitrate or calcium carbonate, are preferred. The organic calcium compounds preferably include calcium lactate, calcium citrate, calcium acetate and calcium fumarate.

As the inorganic phosphoric acid compounds which may be employed in the method of the present invention, those which exhibit high solubility in water and which may be readily reacted with calcium to yield hydroxy apatites are preferably employed, such as phosphoric acid, ammonium phosphate or potassium phosphate. The organic phosphoric acid compounds preferably include phosphoric acid triacetic acid, DL-O-phosphoserine, and O-phospho-L-tyrosine.

On the other hand, the additives which may be employed in the method of the present invention preferably include organic compounds which may be reacted with calcium in the calcium phosphate compounds or the calcium compounds to yield calcium salt compounds. Among these organic compounds are hydroxycarboxylic acids, such as citric acid or lactic acid, and amino carboxylic acids, such as EDTA (ethylenediamine tetraacetic acid) or CyDTA (cyclohexanediamine tetraacetic acid).

In the method for the preparation of apatite whisker according to the present invention, a liquid containing phosphoric acid and calcium is prepared. More specifically, a slurry of a calcium phosphate compound containing additive(s) (referred to hereinafter as slurry 1) or a solution thereof (referred to hereinafter as solution 1); a mixed slurry of inorganic calcium compound(s), additive(s) and inorganic phosphoric acid compound(s) (referred to hereinafter as slurry 2) or a solution thereof (referred to hereinafter as solution 2); a mixed slurry of organic calcium compound(s) and inorganic phosphoric acid compound(s) (referred to hereinafter as slurry 3) or a solution thereof (referred to as a solution 3); or a mixed slurry of organic phosphoric acid compound(s) and inorganic calcium compound(s) (referred to hereinafter as slurry 4) or a solution thereof (referred to hereinafter as solution 4) is prepared.

The slurry 1 or the solution 1 may be prepared by agitating and mixing the calcium phosphate compound(s) in water to yield a slurry or solution and by adding the above mentioned additive(s) to the resulting slurry 1 or solution 1 in an amount of 1 to 50 wt. % based on the total weight of the produced slurry 1 or solution 1. The ratio of the calcium phosphate compound(s) to water in the slurry 1 or solution 1 may preferably be in the range of from 1:1 to 100 by weight. It is noted that the state of the slurry 1 in which the calcium phosphate compound(s) and the additive(s) are substantially dissolved is the solution 1.

The slurry 2 or the solution 2 may be prepared by agitating and mixing the inorganic phosphoric acid compound(s) and the additive(s) in water, adding the inorganic calcium compound(s) to the resulting mixture and by further agitating and mixing the resulting product. The amount of addition of the additive(s) may preferably be 1 to 50 wt. % based on the total weight of the resulting slurry 2 or solution 2. The mixing ratio of the inorganic calcium compound(s), the inorganic phosphoric acid compound(s) and water in the slurry 2 or the solution 2 may preferably be in the range of from 1:0.1 to 1:1 to 100 by weight. The state of the slurry 2 in which the inorganic calcium compound(s), the inorganic phosphoric acid compound(s) and the additive(s) are substantially dissolved is the solution 2.

The slurry 3 or 4 or the solution 3 or 4 may be prepared by agitating and mixing the organic calcium compound(s) and the inorganic phosphoric acid compound(s) in water or by agitating and mixing the inorganic calcium compound(s) and the organic phosphoric acid compound(s) in water. The mixing ratio of the organic calcium compound(s) or the inorganic calcium compound(s), the organic phosphoric acid compound(s) or the inorganic phosphoric acid compound(s) and water may preferably be 1:0.1 to 1:1 to 100. The state of the slurry 3 or 4 in which the respective compounds are dissolved substantially is the solution 3 or 4.

Then, in the slurry 1 or 2 or in the solution 1 or 2, a compound produced in the dissolved state by reaction of calcium contained in the calcium phosphate compound(s) or the inorganic calcium compound(s) with the additive(s) is reacted and reprecipitated with phosphoric acid groups remaining in the dissolved state so as to be precipitated and allowed to grow in size to give the apatite whisker of the present invention. In the slurry 3 or 4 or in the solution 3 or 4, calcium in the organic calcium compound(s) or calcium in the inorganic calcium compound(s) is reacted with the inorganic phosphoric acid compound(s) or with the organic phosphoric acid compound(s), respectively to give the apatite whisker of the present invention.

In the method for the preparation of the apatite whisker of the present invention, the carbonic acid groups yielded from a $CO_2$ gas obtained as a decomposition product of organic components in the organic phosphoric acid compound(s) or the organic calcium compound(s), or compounds yielded by the reaction of the calcium phosphate compound(s) or the inorganic calcium compound(s) with the additive(s), may partially be taken into the apatite whisker as an ultimate product for producing the apatite whisker in stability without being affected by pH values.

The method of precipitating apatite to cause the growth of the crystal grains at a mean aspect ratio (the ratio of length along c-axis to that along a-axis) of not lower than 10 may preferably include heating by hydrothermal treatment under a saturation vapor pressure at a temperature not lower than the boiling point of the solvent of the liquid containing phosphoric acid and calcium.

The apatite whisker of the present invention may be purified as conventionally if necessary for application.

Since the apatite whisker of the present invention is allowed to grow selectively along the c-axis of the crystal, that is, along the direction of the a-plane or the b-plane, so that the above-mentioned mean aspect ratio is not less than 10, it may be used as a biotechnological material for selectively increasing the efficiency of separation or cultivation of substances or cells showing affinity with respect to the phosphoric acid groups.

On the other hand, with the apatite whisker of the present invention, since the primary particles are controlled precisely in shape, the whisker exhibits a sufficient mechanical strength when used as a variety of fiber-reinforced composite materials or as a substitution building material for asbestos. The apatite whisker is composed of apatite exhibiting high bioaffinity and hence is not harmful when assimilated into the human bodies. Since the whisker is metabolized physiologically, it is not cancerogenic despite shape stimulation and hence is superior in hygienic safety.

EXAMPLES OF THE INVENTION

The present invention will be explained further with reference to several Examples. It is to be noted that these Examples are given for illustration only and are not intended for limiting the invention.

EXAMPLE 1

10 g of a powder mixture of a synthetic hydroxy apatite and synthetic tricalcium phosphate were suspended in 500 ml of water to produce a slurry. 25 g of citric acid were added to and dissolved in the so-produced slurry and the resulting solution was charged to an autoclave for hydrothermal treatment at 200° C. for 5 hours under a pressure of 2 MPa. The slurry obtained by the hydrothermal treatment was washed with 1 lit. of distilled water, filtered and dried by a dryer at 100° C.

The Ca/P molar ratio and the amount of the carbonic acid groups and a shape of the produced apatite whisker were measured in accordance with the following method. It was found that the Ca/P molar ratio was 1.67 and the amount of the carbonic acid groups was 0.1 wt. % and that, as to the shape, the mean length was 10 $\mu$m, the length along the longer axis was 0.5 $\mu$m and the aspect ratio (the length ratio along c-axis/a-axis) was 20.

For measuring the Ca/P molar ratio, a measurement device XRD manufactured and sold by RIGAKU DENKI KK under the trade name of "RV-200" was employed. For measuring the amount of the carbonic acid groups, the whisker sample was baked in an oxygen gas at a temperature of 1250° C. and the carbonic gas yielded at this time was analyzed with an IR analyzer manufactured and sold by HORIBA SEISAKUSHO KK under the trade name of "EM2A-110". The whisker shape was measured by SEM with a device manufactured and sold by NIPPON DENSHI KK. under the trade name of "T-20".

EXAMPLE 2

25 g of citric acid and 6.89 g of 85 wt. % phosphoric acid were dissolved in 500 ml of water. To the resulting solution there was added and dissolved 7.37 g of calcium hydroxide. The resulting solution was charged to an autoclave and treated hydrothermally for 5 hours at 200° C. at a pressure of 2 MPa. The slurry obtained after the hydrothermal treatment was washed with 1 lit. of distilled water. The washed slurry was filtered and dried at 100° C. by a dryer. The Ca/P molar ratio, the amount of the carbonic acid groups and the shape of the produced apatite whisker were measured in the same manner as in Example 1, as a result of which it was found that the Ca/P molar ratio was 1.65 and the amount of the carbonic acid groups was 0.1 wt. %, and that, as to shape, the mean length was 20 $\mu$m, the length along the long axis was 0.5 $\mu$m, and the aspect ratio (length along c-axis/length along a-axis) was 40.

EXAMPLE 3

30.68 g of calcium lactate were dissolved in 500 ml of water. 6.88 g of phosphoric acid were mixed and dissolved in the resulting solution. The resulting mixed solution was charged into an autoclave for hydrothermal treatment for 5 hours at 200° C. at a pressure of 2 MPa. The slurry obtained after the hydrothermal treatment was washed with 1 lit. of distilled water. The washed slurry was filtered and dried at 100° C. by a dryer. The Ca/P molar ratio, the amount of the carbonic acid groups and the shape of the produced apatite whisker were measured in the same manner as in Example 1, as a result of which it was found that the Ca/P molar ratio was 1.66 and the amount of the carbonic acid groups was 0.05 wt. % and that, as to shape, the mean length was 1 $\mu$m, the length along the long axis was 0.1 $\mu$m and the aspect ratio (length along c-axis/length along a-axis) was 10.

EXAMPLE 4

16.23 g of phosphoric acid triacetic acid [(HOOCC-H$_2$O)$_3$PO] were dissolved in 500 ml of water. 7.36 g of calcium hydroxide were mixed and dissolved in the resulting solution. The resulting mixed solution was charged into an autoclave for hydrothermal treatment for 5 hours at 200° C. at a pressure of 2 MPa. The slurry obtained after the hydrothermal treatment was washed with 1 lit. of distilled water. The washed slurry was filtered and dried at 100° C. by a dryer. The Ca/P molar ratio, the amount of the carbonic acid groups and the shape of the produced apatite whisker were measured in the same manner as in Example 1, as a result of which it was found that the Ca/P molar ratio was 1.65 and the amount of the carbonic acid groups was 0.05 wt. %, and that, as to the shape, the mean length was 5 $\mu$m, the length along the longer axis was 0.3 $\mu$m and the aspect ratio (length along c-axis/length along a-axis) was 15.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A hydroxyapatite whisker having a mean aspect ratio (length along c-axis/length along a-axis) of not less than 10.0 and containing a carbonic acid group of not less than 0.01 wt. % based on total weight of the whisker.

2. The whisker as claimed in claim 1 wherein said length along said a-axis is 0.1 to 10 $\mu$m and that along said c-axis is 1 to 1000 $\mu$m.

3. The whisker as claimed in claim 1 wherein the carbonic acid group is contained in amount up to 5 wt. % based on total weight of the whisker.

4. A method for preparing a hydroxyapatite whisker comprising precipitating and growing a hydroxyapatite containing a carbonic acid group of not less than 0.01 wt. % based on total weight of the whisker from a liquid containing phosphoric acid and an elemental calcium-containing compound in the presence of a CO$_2$ gas to have a mean aspect ratio (length along c-axis/length along a-axis) of not less than 10.0.

5. The method according to claim 4 wherein said liquid is selected from the group consisting of a slurry of a calcium phosphate compound containing an additive; a solution of a calcium phosphate compound containing an additive; a mixed slurry of an inorganic calcium compound, an additive and an inorganic phosphoric acid compound; a mixed solution of an inorganic calcium compound, an additive and an inorganic phosphoric acid compound; a mixed slurry of an organic calcium compound and an inorganic phosphoric acid compound; a mixed solution of an organic calcium compound and an inorganic phosphoric acid compound; a mixed slurry of an organic phosphoric acid compound and an inorganic calcium compound; and a mixed solution of an organic phosphoric acid compound and an inorganic calcium compound, said additive being selected from the group consisting of citric acid, lactic acid, amino carboxylic acid and mixtures thereof.

6. The method as claimed in claim 5 wherein said calcium phosphate compound is selected from the group consisting of hydroxyapatite, tricalcium phosphate, monetite, brucite and mixtures thereof.

7. The method as claimed in claim 5 wherein said inorganic calcium compound is selected from the group consisting of calcium hydroxide, calcium nitrate, calcium carbonate and mixtures thereof.

8. The method as claimed in claim 5 wherein said organic calcium compound is selected from the group consisting of calcium lactate, calcium citrate, calcium acetate, calcium fumarate and mixtures thereof.

9. The method according to claim 5 wherein said inorganic phosphoric acid compound is selected from the group consisting of phosphoric acid, ammonium phosphate, potassium phosphate and mixtures thereof.

10. The method according to claim 5 wherein said organic phosphoric acid compound is selected from the group consisting of phosphoric acid triacetic acid, DL-O-phosphoserine, O-phospho-L-tyrosine and mixtures thereof.

11. The method as claimed in claim 5 wherein a mixing ratio of said additive in said slurry and solution is 1 to 50 wt. %.

12. The method as claimed in claim 5 wherein the slurry and the solution of the calcium phosphate compound containing the additive are prepared by mixing the calcium phosphate compound in water under agitation followed by addition of the additive.

13. The method as claimed in claim 12 wherein a mixing ratio of said calcium phosphate compound to water is 1:1 to 100 by weight.

14. The method as claimed in claim 5 wherein the mixed slurry and solution of said inorganic calcium compound, the additive and the inorganic phosphoric acid compound are prepared by mixing the inorganic phosphoric acid compound and the additive in water under agitation followed by addition of the inorganic calcium compound.

15. The method as claimed in claim 14 wherein a mixing ratio of said inorganic calcium compound, the inorganic phosphoric acid compound and water is 1:0.1 to 1:1 to 100 by weight.

16. The method as claimed in claim 5 wherein the mixed slurry and solution of the organic calcium compound and the inorganic phosphoric acid compound, and the mixed slurry and solution of said organic phosphoric acid compound and the inorganic calcium compound are prepared by mixing in water under agitation.

17. The method as claimed in claim 16 wherein a mixing ratio of the organic calcium compound, the inorganic phosphoric acid compound and water is 1:0.1 to 1:1 to 100 by weight.

18. The method as claimed in claim 16 wherein a mixing ratio of the inorganic calcium compound, the organic phosphoric acid compound, and water is 1:0.1 to 1:1 to 100 by weight.

19. The method as claimed in claim 4 wherein said hydroxyapatite is precipitated and grown in size from said liquid by hydrothermal treatment under a saturated vapor pressure at a temperature not lower than a boiling point of a solvent of said liquid.

* * * * *